United States Patent [19]  [11] 4,267,112
Reusser et al.  [45] May 12, 1981

[54] ANTIBIOTIC U-58,431

[75] Inventors: Fritz Reusser, Portage; Libor Slechta, Kalamazoo, both of Mich.

[73] Assignee: The Upjohn Company, Kalamazoo, Mich.

[21] Appl. No.: 79,446

[22] Filed: Sep. 27, 1979

Related U.S. Application Data

[63] Continuation of Ser. No. 34,247, Apr. 30, 1979, abandoned.

[51] Int. Cl.$^3$ ............................................. C07D 311/74
[52] U.S. Cl. .................. 260/345.2; 435/117; 435/253; 424/118
[58] Field of Search ...................... 260/345.2; 424/118

[56] References Cited

U.S. PATENT DOCUMENTS 4,027,014 5/1977 Ezaki et al. ........................... 424/122

*Primary Examiner*—Nicky Chan

[57] ABSTRACT

Novel antibiotic U-58,431 producible in a fermentation under controlled conditions using a biologically pure culture of the microorganism *Streptomyces helicus* Dietz and Li sp. n., NRRL 11461. This antibiotic is active against various Gram-positive bacteria, for example, *Staphylococcus aureus*, *Streptococcus hemolyticus*, and *Streptococcus faecalis*. It is also active against various Gram-negative bacteria, for example, *Escherichia coli*, *Proteus vulgaris*, *Klebsiella pneumoniae*, *Pseudomonas aeruginosa*, and *Salmonella schottmuelleri*. It has strong activity against *Diplococcus pneumoniae*. Thus, antibiotic U-58,431 can be used in various environments to eradicate or control such bacteria.

4 Claims, 1 Drawing Figure

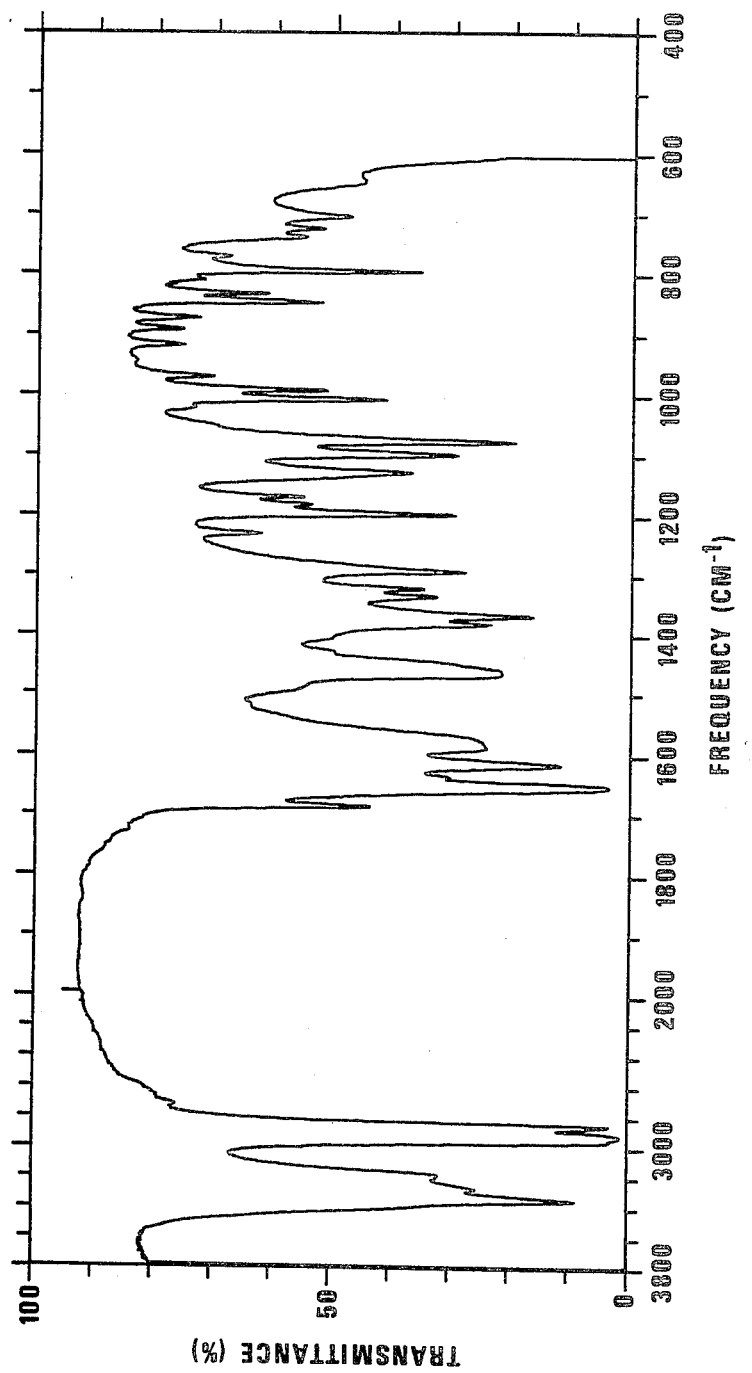

ANTIBIOTIC U-58,431

CROSS REFERENCE TO RELATED APPLICATION

This is a continuation of application Ser. No. 34,247, filed Apr. 30, 1979, now abandoned.

BRIEF SUMMARY OF THE INVENTION

Antibiotic U-58,431 is producible in a fermentation under controlled conditions using a biologically pure culture of the new microorganism *Streptomyces helicus* Dietz and Li sp.n., NRRL 11461.

Antibiotic U-58,431 is active against various Gram-positive and Gram-negative bacteria. Further, the base addition salts of antibiotic U-58,431 are also active against these bacteria. Thus, antibiotic U-58,431 and its salts can be used to disinfect washed and stacked food utensils contaminated with *S. aureus*. They can also be used as disinfectants on various dental and medical equipment contaminated with *S. aureus*. Since antibiotic U-58,431 and its salts are active against *P. vulgaris*, they can be used as an oil preservative to inhibit this bacterium which is known to cause spoilage in oil. Still further, antibiotic U-58,431 and its salts can be used as a bacteriostatic rinse for laundered cloths, and for impregnating papers and fabrics; and, they are also useful for suppressing the growth of sensitive organisms in plate assays and other microbiological media.

DETAILED DESCRIPTION OF THE INVENTION

Chemical and Physical Properties of Antibiotic U-58,431:

Molecular Weight: 294.0843 (high resolution spectrometry).
Molecular Formula: $C_{13}H_{14}N_2O_6$
Elemental Analysis: C, 52.70; H, 5.40; N, 9.45.
Ultraviolet Absorption Spectrum:
The solution of antibiotic U-58,431 in methanol displayed absorption as follows:

| λ max | Absorbance | Absorptivity ($\epsilon$) |
|---|---|---|
| 261 | 44.80 | 13,250 |
| 472 | 5.16 | 1,550 |

No shifts in acid or base.
Melting point: 155.9° C. to 157.3° C. with decomposition.
Infrared Absorption Spectrum:
Antibiotic U-58,431 has a characteristic infrared absorption spectrum in a mineral oil mull as shown in the drawing. Peaks are observed at the following wave lengths expressed in reciprocal centimeters.

| Band Frequency (Wave Numbers) | Intensity |
|---|---|
| 3355 | S |
| 3280 | S |
| 3190 | S |
| 2960 | S |
| 2925 | S |
| 2850 | S |
| 2730 | W |
| 1685 | M |
| 1650 | S |
| 1635 | S |
| 1614 | S |
| 1587 | S |
| 1577 | S, sh |
| 1487 | M, sh |
| 1463 | S |
| 1428 | M, sh |
| 1402 | M, sh |
| 1377 | S |
| 1364 | S |
| 1331 | M |
| 1318 | M |
| 1290 | S |
| 1228 | M |
| 1195 | S |
| 1180 | M |
| 1168 | M |
| 1125 | M |
| 1095 | S |
| 1073 | S |
| 1020 | W |
| 1003 | M |
| 990 | M |
| 967 | W |
| 915 | W |
| 888 | W |
| 869 | W |
| 843 | M |
| 828 | M |
| 805 | W |
| 791 | M |
| 767 | W |
| 734 | M |
| 720 | M |
| 700 | M |
| 642 | M |

Key:
S = Strong
M = Medium
W = Weak
sh = shoulder

Solubilities

Antibiotic U-58,431 is soluble in water, methanol, and ethanol, and slightly soluble in cold methylene chloride and chloroform.

Antimicrobial Spectrum Of Antibiotic U-58,431

Antibiotic U-58,431 is active against various Gram-positive and Gram-negative bacteria and fungi as shown in the following tables.

Assay

The antibacterial assay is a standard microbiological broth assay. The MIC is determined by standard methods using two-fold dilutions of the antibiotic in Brian Heart Infusion Broth (Difco Lab., Detroit, Michigan). The inocula are overnight cultures of the test organisms, diluted so that the final population contains approximately $10^5$ cells/ml. The tubes are incubated at 28° to 37° C. for 42 hours. The lowest antibiotic concentration which allows no growth=MIC or minimum inhibitory concentration.

| Microorganism | Minimum Inhibitory Concentration (mcg/ml) |
|---|---|
| Staphylococcus aureus 284 UC 76 | 125 |
| Staphylococcus aureus UC 570 | 125 |
| Staphylococcus aureus UC 746 | 125 |
| Streptococcus hemolyticus UC 152 | 125 |
| Streptococcus faecalis UC 694 | 250 |
| Escherichia coli UC 45 | 250 |

-continued

| Microorganism | Minimum Inhibitory Concentration (mcg/ml) |
|---|---|
| *Proteus vulgaris* UC 93 | 250 |
| *Klebsiella pneumoniae* UC 58 | 125 |
| *Salmonella schottmuelleri* UC 126 | 62.5 |
| *Pseudomonas aeruginosa* UC 95 | 125 |
| *Diplococcus pneumoniae* UC 41 | 1.0 |

The antifungal spectrum for antibiotic U-58,431 was conducted on a standard agar difusion assay. The results are as follows:

| Test Organisms | Results At Indicated Concentration (mcg/ml) | | | |
|---|---|---|---|---|
| | 1000 | 100 | 10 | 1 |
| *Nocardia asteroides* UC 2052 | − | + | + | + |
| *Blastomyces dermatidis* UC 1466 | + | + | + | + |
| *Geotrichum* sp. UC 1207 | + | + | + | + |
| *Hormodendrum compactum* UC 1222 | + | + | + | + |
| *Cryptococcus neoformans* UC 4869 | + | + | + | + |
| *Cryptococcus neoformans* UC 1139 | + | + | + | + |
| *Sporotrichum schenckii* UC 1364 | + | + | + | + |
| *Candida albicans* UC 7163 | + | + | + | + |
| *Candida albicans* UC 7164 | + | + | + | + |
| *Trichophyton rubrum* UC 1458 | − | + | + | + |
| *Trichophyton violaceum* UC 1459 | + | + | + | + |
| *Trichophyton asteroides* UC 4775 | + | + | + | + |
| *Trichophyton mentagrophytes* UC 4797 | − | + | + | + |
| *Trichophyton mentagrophytes* UC 4860 | + | + | + | + |

Key:
− = inhibition
+ = no inhibition

"UC" is a registered trademark of The Upjohn Company Culture Collection. These cultures can be obtained from The Upjohn Company in Kalamazoo, Michigan, upon request.

Antifungal in vitro Method
Method for Antifungal Testing

An agar dilution method is used. 100 mg amounts of material is solubilized in 1 ml of dimethylformamide (DMF) and diluted to 10 ml with mycophil Broth (BBL labs.) unless completely soluble in water. The material to be tested is incorporated in melted (48° C.) mycophil Agar at concentrations of 1000, 100, 10 and 1 mcg/ml. Fifteen ml of agar is pipetted into a petri dish. After solidification, the surface is streaked with agar spore suspensions of human fungal pathogens. The suspensions are made by adding 10 ml sterile distilled water to agar slants of the test organisms. The slant surface is scraped with a sterile inoculating needle, and 0.5 ml of this suspension is added to 9.5 ml melted (48° C.) mycophil Agar in a stamp streak well. (Each stamp streak base has 6 wells.)

The streaked plates are incubated at 28° C. for 72 hours at which time results are recorded. Readings are by visual observation.

THE MICROORGANISM

The microorganism used for the production of antibiotic U-58,431 is a biologically pure culture of *Streptomyces helicus* Dietz and Li sp. n., NRRL 11461.

A subculture of this microorganism can be obtained from the permanent collection of the Northern Regional Research Laboratory, U.S. Department of Agriculture. Peoria, Illinois, U.S.A. Its accession number in this depository is NRRL 11461. It should be understood that the availability of the culture does not constituted a license to practice the subject invention in derogation of patent rights granted with the subject instrument by governmental action.

The microorganism of this invention was studied and characterized by Alma Dietz and Grace P. Li of The Upjohn Research Laboratories.

The culture characterized is considered to be a new species of Streptomyces for which the designation proposed is *Streptomyces helicus* Dietz and Li sp. n. It is understood that this new type species is to be designated the type subspeices, should a variant be found. This is in accordance with the rules set forth in the International Code of Nomenclature of Bacteria [Lapage, S.P., et al. eds. 1975. International Code of Nomenclature of Bacteria (Bacteriological Code, 1976 Revision). ASM, Wash., D.C.].

The culture is differentiated from *Streptomyces olivaceus* ATCC 3335 and *Streptomyces griseoroseus* ATCC 12125.

The methods used in characterizing the culture were modifications of those cited in Dietz [Dietz, A. 1954. Ektachrome transparencies as aids in actinomycete classification. Ann. N.Y. Acad. Sci. 60: 152-154.] [Dietz, A. 1967. *Streptomyces steffisburgensis* sp. n. J. Bacteriol. 94: 2022-2026.], Dietz and Mathews [Dietz, A., and J. Matthews. 1970. Classification of Streptomyces spore surfaces into five groups. Appl. Microbiol. 21: 527-533.], and Shirling and Gottlieb [Shirling, E. B., and D. Gottlieb. 1966. Methods for characterization of Streptomyces species. International Journal of Systematic Bacteriology. 16: 313-340].

*Streptomyces helicus* Dietz and Li sp.n., NRRL 11461, a new soil isolate, appeared similar to *Streptomyces olivaceus* ATCC 3335 [Shirling, E. B., and D. Gottlieb. 1968. Cooperative description of type cultures of Streptomyces. II. Species descriptions from first study. Int. J. Syst. Bacteriol. 18: 69-189.] [Waksman, S. A. 1961. The actinomycetes. Vol. II. Classification identification and descriptions of genera and species. The Williams & Wilkins Co., Baltimore, MD, 363 pp.] and *Streptomyces griseoroseus* ATCC 12125 [Hütter, R. 1967. Systematik der Streptomycetan unter besonderer Berücksichtigung der von ihnen gebildeten Antibiotic. S. Karger, Basel and New York, 382 pp.] [Walker, J. E., M. Bodanszky, and D. Perlman. 1970. The biogenetic origin of the N-methyl-γ-methyl-L-isoleucine residue of etamycin. J. Antibiotics. XXIII: 255-256.] by comparison on Ektachrome [Dietz, A. 1954. Ektachrome transparencies as aids in actinomycete classification. Ann. N.Y. Acad. Sci. 60: 152-154.]. All showed long straight to open spiral to spiral spore chains when observed by light microscopy and scanning electron microscopy (SEM). All had oval-shaped smooth spores with a depressed or ridged surface. (This was determined by SEM). The new culture had a greater number of spore chains with helical tips than the cultures with which it was compared. Other differences are given in Tables 2-5. The most distinctive differences are in reverse color, gelatin liquefaction, nitrate reduction, reactions in litmus milk and growth on carbon compounds in synthetic medium.

The cultures also differ in their antibiotic-producing properties. *S. olivaceus* shows little or no antagonistic properties in our media. The production of etamycin [Lapage, S. P. spura] [Walker, J. E. surpra] by *S. griseoroseus* has been confirmed. The new culture produces the antibiotic U-58,431.

The new culture may be placed in the Red series of Pridham and Tresner in Bergey's Manual, 8th ed. [Buchanan, R. E., and N. E. Gibbons, eds. 1974. Bergey's manual of determinative bacteriology, 8th Ed. The Williams & Wilkins Co., Baltimore, MD. 1246 pp.] based on surface color reading with the color chip system of Tresner and Backus [Tresner, H. D., and E. J. Backus, 1963. System of color wheels for streptomycete taxonomy. Applied Microbiol. 11: 335-338.]. The new culture is distinguished from the cultures cited for the Red series. The Gray series may also be considered since *S. olivaceus* which was characterized in the International Streptomyces Project [Shirling, E. B., and D. Gottlieb. 1968. Cooperative description of type culture of Streptomyces. II. Species descriptions from first study. Int. J. Syst. Bacteriol. 18: 69-189.] is placed in this series. The new culture differs from cultures in this series. This conclusion is based on comparison of our results with those in Bergey's Manual.

Color characteristics: Aerial growth lavender gray. Melanin negative. The appearance of the culture on Ektachrome [Buchanan, R. E. supra] is given in Table 1. Reference color characteristics are given in Table 2. The culture may be placed in the (R) Red color series of Tresner and Backus [supra].

Microscopic characteristics: The spore chains, observed with the light microscope and the scanning electron microscope, are long, flexuous to open spiral to spiral. The spore surface, as observed with the scanning electron microscope, is smooth with ridges or depressions.

Cultural and biochemical characteristics: These are given in Table 3.

Carbon utilization: See Tables 4 and 5.

Temperature: The culture grew well at 18°-37° C. on Bennett's, Czapek's sucrose, and maltose-tryptone agars.

TABLE 1

Ektachrome Comparison Of *S. helicus*, *S. olivaceus* ATCC 3335, And *S. griseoroseus* ATCC 12125

| Agar Medium | | *S. helicus* | *S. olivaceus* | *S. griseoroseus* |
|---|---|---|---|---|
| Bennett's | S | Trace gray | Trace gray | Very slight trace gray |
| | R | Pale yellow | Yellow-tan | Tan |
| Czapek's sucrose | S | Lavender-gray | Pale gray | Pale lavender-gray |
| | R | Pale gray | Colorless | Colorless |
| Maltose-tryptone | S | Lavender-gray | Lavender-gray | Gray-salmon |
| | R | Light red-brown | Gray-tan | Red-brown |
| Peptone-iron | S | Colorless | Colorless | Colorless |
| | R | Tan | Tan | Tan |
| 0.1% Tryosine | S | Colorless | Colorless | Colorless |
| | R | Red | Pale red | Red |
| Casein starch | S | Colorless | Colorless | Colorless |
| | R | Colorless | Colorless | Light tan |

S = Surface
R = Reverse

TABLE 2

Reference Color Characteristics [NBS Color Chips*]

| Agar Medium | Determination | *S. helicus* | *S. olivaceus* | *S. griseoroseus* |
|---|---|---|---|---|
| Bennett's | S | 60 l.gy.Br = light grayish brown | 31 p.y. Pink = pale yellowish pink | 32 gy.y Pink = Grayish yellowish pink |
| | R | 109 l.gy.Ol = light grayish olive | 77 m.y. Br = moderate yellowish brown | 57 l.Br = light brown |
| | P | 106 l.Ol = light olive | — | 57 l.Br = light brown |
| Czapek's sucrose | S | 33 br Pink = brownish pink | 31 p.y. Pink = pale yellowish pink | 31 p.y. Pink = pale yellowish pink |
| | R | 68 s. OY = strong orange yellow | 73 p. OY = pale orange yellow | 73 p. OY = pale orange yellow |
| | P | — | — | — |
| Maltose-tryptone | S | 32 gy.y Pink = grayish yellowish pink | 31 p.y. Pink = pale yellowish pink | 33 br Pink = brownish pink |
| | R | 87 m.Y = moderate yellow | 77 m.y Br = moderate yellowish brown | 65 br Black = brownish black |
| | P | 106 l.Ol = light olive | — | 59 d. Br = dark brown |
| Yeast extract-malt extract (ISP-2) | S | 33 br Pink = brownish pink | 60 l.gy.Br = light grayish brown | 31 p.y Pink = pale yellowish pink |
| | R | 114 Ol Black = olive black | 77 m.y Br = moderate yellowish brown | 58 m. Br = moderate brown |
| | P | 151 d.gy.G = dark grayish green | — | 77 m.y Br = moderate yellowish brown |
| Oatmeal (ISP-3) | S | 33 br Pink = brownish pink | 60 l.gy. Br = light grayish brown | 31 p.y Pink = pale yellowish pink |
| | R | 67 brill. OY (center) = brilliant orange yellow | 77 m.y. Br = moderate yellowish brown | 73 p. OY = pale orange yellow |
| | | 16 d.R. (edge) = dark red | | |
| | P | 8 gy. Pink = grayish pink | — | 73 p. OY = pale orange yellow |
| Inorganic-salts starch (ISP-4) | S | 60 l.gy. Br = light grayish brown | 60 l.gy. Br = light grayish brown | 31 p.y. Pink = pale yellowish pink |
| | R | 75 deep y Br = deep yellowish brown | 70 l. OY = light orange yellow | 65 br Black = brownish black |
| | P | 8 gy. Pink = grayish pink | — | 57 l. Br = light brown |
| Glycerol-asparagine (ISP-5) | S | 60 l.gy. Br = light grayish brown | 60 l.gy. Br = light grayish brown | 31 p.y Pink = pale yellowish pink |
| | R | 188 bk blue = blackish blue | 70 l. OY = light orange yellow | 58 m. Br = moderate brown |
| | P | 187 d.gy. blue = dark | — | 57 l.Br = light |

TABLE 2-continued

| | | Reference Color Characteristics [NBS Color Chips*] | | |
|---|---|---|---|---|
| Agar Medium | Determination | S. helicus | S. olivaceus | S. griseoroseus |
| | | grayish blue | | brown |

S = Surface
R = Reverse
P = Pigment
*SP 440. Color: Universal Language and Dictionary of Names. U.S. Government Printing Office, Washington, D.C. 20402. SRM 2106. ISCC-NBS Centroid Color Charts. Office of Standard Reference Material, Room B311, Chem. Bldg., National Bureau of Standards, Washington, D.C. 20234.

TABLE 3

| | | Cultural and Biochemical Characteristics | | |
|---|---|---|---|---|
| Medium Agar | Determination | S. helicus | S. olivaceus | S. griseoroseus |
| Peptone-iron | S | Greenish tan vegetative growth | Greenish tan vegetative growth | Tan vegetative growth |
| | R | Greenish tan | Yellowish tan | Tan |
| | P | — | Yellow | Tan |
| | O | Melanin negative | Melanin negative | Melanin negative |
| Calcium malate | S | Gray-white | Gray-white | Pink-orange |
| | R | Gray-white | Gray-white | White |
| | P | — | — | — |
| | O | Malate solubilized | Malate solubilized | Malate partially solubilized |
| Glucose asparagine | S | Gray-tan with yellow edge | Gray | Pink-orange |
| | R | Yellow | Light yellow-tan with dark green-tan edge | Brown |
| | P | — | — | — |
| Skim milk | S | Gray-white with yellow edge | Gray | Pink-orange |
| | R | Orange-yellow | Yellow-tan | Orange-tan |
| | P | Yellow-tan | Yellow-tan | Orange-tan |
| | O | Casein solubilized | Casein solubilized | Casein solubilized |
| Tyrosine | S | Gray-white | Gray | Gray-pink |
| | R | Red-tan | Red-tan | Dark red-brown |
| | P | Red-tan | Red-tan | Dark red-tan |
| | O | Tyrosine solubilized | Tyrosine solubilized | Tyrosine solubilized |
| Xanthine | S | Gray-white | Gray-beige | Gray-pink |
| | R | Light yellow | Yellow-tan | Yellow-tan |
| | P | Light yellow | — | — |
| | O | Xanthine solubilized | Xanthine solubilized | Xanthine solubilized |
| Nutrient starch | S | Gray-white | Gray-beige | Gray-pink |
| | R | Light yellow | Yellow-tan | Tan |
| | P | — | — | — |
| | O | Starch solubilized | Starch partially solubilized | Starch partially solubilized |
| Yeast extract-malt extract | S | Gray | Gray-beige | Gray-pink |
| | R | Dark gray-tan | Tan | Red-brown |
| | P | Yellow | — | Red-brown |
| Peptone-yeast extract-iron (ISP-6) | S | Pale greenish-tan vegetative growth | Yellow-tan vegetative growth | Pale yellow-tan vegetative growth |
| | R | Pale greenish-tan | Yellow-tan | Pale yellow-tan |
| | P | Pale greenish-tan | Yellow-tan | Pale yellow-tan |
| | O | Melanin negative | Melanin negative | Melanin negative |
| Tyrosine (ISP-7) | S | Pale lavender-pink | Pale lavender-gray | Heavy cream-pink |
| | R | Pale yellow-pink maroon | Pale cream-gray | Maroon-tan |
| | P | Trace pale pink-tan | — | Pale maroon-tan |
| | O | Melanin negative | Melanin negative | Melanin negative |
| Gelatin | | | | |
| Plain | S | Colorless vegetative | Colorless vegetative | Colorless vegetative |
| | P | — | — | — |
| | O | None to very slight liquefaction | No liquefaction | Complete liquefaction |
| Nutrient | S | Colorless vegetative | Colorless vegetative | Trace cream aerial on surface growth |
| | P | — | — | — |
| | O | Liquefaction complete | No liquefaction | Liquefaction complete |
| Nitrate Broth | | | | |
| Synthetic | S | — | Partial pellicle | Partial pellicle |
| | P | — | — | — |
| | O | Nitrates reduced to nitrites | Nitrates not reduced | Nitrates not reduced |
| Nutrient | S | Light gray-cream aerial on surface ring and pellicle | Light gray-cream aerial on surface ring | Cream-pink aerial on surface pellicle |
| | P | — | — | — |

TABLE 3-continued

Cultural and Biochemical Characteristics

| Medium Agar | Determination | S. helicus | S. olivaceus | S. griseoroseus |
|---|---|---|---|---|
| | O | Poor, compact bottom growth | Compact bottom growth | Compact to flocculent bottom growth |
| | | Nitrates reduced to nitrites | Nitrates not reduced | Nitrates not reduced |
| Litmus milk | S | Orange-tan surface ring | Blue-gray aerial growth on blue-gray surface ring | Maroon surface ring |
| | P | — | Blue-gray | Deep purple |
| | O | No peptonization pH 5.9 | Peptonization pH 7.5 | Slight peptonization pH 6.4 |

S = Surface
R = Reverse
P = Pigment
O = Other Characteristics

TABLE 4.

Growth On Carbon Compounds In The Synthetic Medium Of Pridham And Gottlieb*

| CONTROL | | S. helicus (+) | S. olivaceus (+) | S. griseoroseus (+) |
|---|---|---|---|---|
| 1. | D-xylose | + | + | + |
| 2. | L-arabinose | + | + | + |
| 3. | Rhamnose | + | + | + |
| 4. | D-fructose | + | + | + |
| 5. | D-galactose | + | + | + |
| 6. | D-glucose | + | + | + |
| 7. | D-mannose | + | + | + |
| 8. | Maltose | + | + | + |
| 9. | Sucrose | (+) | + | (+) |
| 10. | Lactose | + | + | + |
| 11. | Cellobiose | + | + | + |
| 12. | Raffinose | (+) | (+) | (+) |
| 13. | Dextrin | + | + | + |
| 14. | Inulin | (+) | + | (+) |
| 15. | Soluble starch | + | + | + |
| 16. | Glycerol | + | + | + |
| 17. | Dulcitol | (+) | (+) | (+) |
| 18. | D-Mannitol | + | + | + |
| 19. | D-Sorbitol (−) | (−) | (+) | |
| 20. | Inositol | + | + | (+) |
| 21. | Salicin | (+) | (+) | + |
| 22. | Phenol | − | − | − |
| 23. | Cresol | − | − | − |
| 24. | Na formate | (−) | (−) | (−) |
| 25. | Na oxalate | (+) | (−) | (+) |
| 26. | Na tartrate | (+) | (+) | (+) |
| 27. | Na salicylate | − | − | − |
| 28. | Na acetate | (+) | (+) | + |
| 29. | Na citrate | (+) | (+) | (+) |
| 30. | Na succinate | (+) | (+) | (+) |

+ = Good growth
(+) = Moderate growth
(−) = Poor growth
− = No growth.
*Pridham, T.G., and D. Gottlieb. 1948. The utilization of carbon compounds by some Actinomycetales as an aid for species determination. J. Bacteriol. 56: 107–114.

TABLE 5

Utilization Of Carbon Compounds In The Synthetic Medium Of Shirling And Gottlieb*

| ISP #9 | S. helicus | S. olivaceus | S. griseoroseus |
|---|---|---|---|
| CONTROL | | | |
| Negative (No carbon compound added) | ± | − | − |
| Positive (D-glucose) | + | + | + |
| Carbon Compounds | | | |
| L-Arabinose | + | + | ++ |
| Sucrose | ± | − | − |
| D-xylose | ++ | ++ | ++ |
| Inositol | + | ++ | ± |
| D-Mannitol | ++ | ++ | ++ |
| D-Fructose | ++ | ++ | ++ |
| Rhamnose | ++ | ++ | ++ |
| Raffinose | ± | − | − |
| Cellulose | ± | − | − |

++ Strong utilization
± Doubtful utilization
+ Positive utilization
− No utilization
*Shirling, E.B., and D. Gottlieb. 1966. Methods for characterization of Streptomyces species. Int. J. Syst. Bacteriol. 16: 313–340.

The compound of the invention process is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound by the invention process can be effected at any temperature conductive to satisfactory growth of the microorganism, for example, between about 18° and 40° C., and preferably between about 20° and 28° C. Ordinarily, optimum production of the compound is obtained in about 3 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by extraction with solvents such as methylene chloride, acetone, butanol, ethyl acetate and the like; and silica gel chromatography can be used to purify crude preparations of the antibiotic.

In a preferred recovery process the compound produced by the subject process is recovered from the culture medium by separation of the mycelia and undissolved solids by conventional means, such as by filtration or centrifugation and solvent extraction of both mycelial cake and clarified broth. The mycelial cake can be extracted with a lower alcohol (1 to 4 carbon atoms, inclusive), methanol (preferred) and the extract evaporated under reduced pressure to an aqueous concentrate. The aqueous concentrate is added to the filtered broth, which then can be extracted three times with a half volume of a lower alcohol, 1-butanol is preferred. The combined preparations are purified by chromatography on silica gel. The active fractions from the column after removal of the solvent yields a red material which is crystallized from boiling chloroform to yield antibiotic U-58,431. The solvent system used for the chromatography is chloroform:methanol (9:1).

The antibiotic of the subject invention also can be recovered from fermentation broth by resin sorption on a resin comprising a non-ionic macro porous copolymer of styrene cross linked with divinylbenzene. Suitable resins are Amberlite XAD-2 and XAD-4, according to the procedure disclosed in U.S. Pat. No. 3,515,717. (Amberlite resins are available from Rohm and Haas, Philadelphia, Pa.). The antibiotic can be eluted from said resin by a water-lower alcohol (preferably methanol) mixture or a water-acetone mixture.

Salts of antibiotic U-58,431 also can be formed with inorganic or organic bases. Such salts can be prepared, as for example, by dissolving antibiotic U-58,431 in water, adding a dilute base until the pH of the solution is about 10.0 to 11.0, and freeze-drying the solution to provide a dried residue consisting of the U-58,431 salt. Antibiotic U-58,431 salts with inorganic cations which can be formed include the sodium, potassium, and calcium salts. Other salts of U-58,431, including those with bases such as primary, secondary, and tertiary monoamines as well as with polyamines, also can be formed using the above-described or other commonly employed procedures. Other valuable salts are obtained with therapeutically effective bases which impart additional therapeutic effects thereto. Such bases are, for example the purine bases such as theophyllin, theobromin, caffeine, or derivatives of such purine bases; antihistaminic bases which are capable of forming salts with weak acids, pyridine compounds such as nicotinic acid amide, isonicotinic acid hydrazide, and the like; phenylalkylamines such as adrenaline, ephedrine, and the like; choline, and others. Salts of U-58,431 can be used for the same biological purposes as the parent compound.

The following examples are illustrative of the process and product of the invention, but are not to be construed as limiting. All percentages are by weight and all solvent mixture proportions are by volume unless otherwise noted.

EXAMPLE 1

A. Fermentation

A biologically pure culture of *Streptomyces helicus* Dietz and Li sp.n., NRRL 11461, is used to inoculate 500-ml Erlenmeyer seed flasks containing 100 ml of sterile medium consisting of the following ingredients:

| | |
|---|---|
| Glucose monohydrate | 25 g/l |
| Pharmamedia* | 25 g/l |
| Tap water q.s. | 1 liter |

*Pharmamedia is an industrial grade of cottonseed flour produced by Traders Oil Mill Company, Fort Worth, Texas.

The preseed medium presterilization pH is 7.2. The preseed inoculum is grown for three days at 28° C. on a Gump rotary shaker operating at 250 rpm and having a 2½ inch stroke.

Preseed inoculum (300 ml), prepared as described above, is used to inoculate a seed tank containing 20 liters of sterile seed medium consisting of the following ingredients:

| | |
|---|---|
| Glucose monohydrate | 25 g/l |
| Pharmamedia | 25 g/l |
| Tap water | Balance |

The inoculated seed medium is incubated at a temperature of 28° C. for 2 days while being agitated at a rate of 400 rpm and aerated at a rate of 10 standard liters per minute with a back pressure of 10 psig.

After 2 days incubation, the seed medium is used to inoculate (the inoculation rate is 5 liters of seed inoculum per 100 liters of fermentation medium) a 250 liter tank fermentation containing sterile fermentation medium consisting of the following ingredients:

| | |
|---|---|
| Glucose monohydrate | 15 g/l |
| Dextrin | 25 g/l |
| Corn gluten meal | 20 g/l |
| Oatmeal | 15 g/l |
| Calcium carbonate | 8 g/l |
| Ucon* | 0 3 ml/l | pH - 7.2 (presterilization)
*Ucon is a synthetic defoamer supplied by Union Carbide, New York, New York.

The fermentation tank is incubated at a temperature of 28° C. with agitation of 280 rpm and aeration at 185 standard liters per minute. Harvest is usually after about five days of fermentation. A typical five-day fermentation has the following titers of antibiotic in the fermentation broth:

| Day | Assay. U/ml |
|---|---|
| 1 | 0 |
| 2 | 0 |
| 3 | 0 |
| 4 | 8 |
| 5 | 32 |

The assay is a *Bacillus subtilis* disc plate assay using 0.1 M Tris buffer, pH 7.0 as diluent.

B. Recovery

The whole beer (ca. 3 l) from a fermentation, as described above, is adjusted to pH 5.0 with concentrated HCl and the mycelium removed by filtration through diatomaceous earth (dicalite). To the clear broth (2.7 l) are added 1.2 kg solid $(NH_4)_2SO_4$. After dissolution of the salt, the broth is extracted with 1600 ml 1-butanol. The mycelium cake is mixed with 600 ml of methanol for 1 hour. The suspension is filtered through a dicalite pad; yield 600 ml clear filtrate. The extracts from the clear broth and the mycelial cake are combined at this point and reduced to an oil under vacuum. The oily residue is triturated with 150 ml warm methylene chloride. Insolubles are removed by filtration and the methylene chloride extract is subjected to column chromatography on silica gel. Two hundred grams of silica gel (Merck) is suspended in methylene chloride-methanol (9:1 v/v) and a column 35×3.8 cm is poured. The above methylene chloride extract is taken up in 5 g of dry silica gel and the material is applied to the column. The column is eluted with a methanol-methylene chloride mixture (1:9 v/v). Fractions of 100 ml are collected and assayed vs. *Sarcina lutea* on a standard disc assay. Fraction 7 contains most of the activity and is reduced to approximately 4 ml under vacuum. The concentrated solution is allowed to stand at 4° C. overnight and the crystals of antibiotic U-58,431 formed are recovered by filtration; yield=26 mg. The concentrated crystals are recrystallized from boiling chloroform; yield=10 mg of antibiotic U-58,431.

Initial analysis of antibiotic U-58,431 by X-ray crystallography gives the following structure:

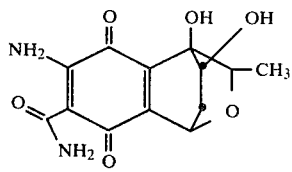

Antibiotic U-58,431 can be acylated at the two hydroxyl and two amino groups. By using a minimum amount of acylating agent the two amino groups are acylated first to give di-N-acylates. Di-O-acylates are obtained by methods known in the art, e.g., protecting the amino groups, acylating the two hydroxyls, then removing the amino protective groups. Tetra acylates are formed by acylating U-58,431 with an excess of acylating agent.

U-58,431 can be acylated under standard acylating conditions with an appropriate acid halide or anhydride to give the acylated compounds. The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, terbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and lower alkoxy- hydrocarbon carboxylic acids include hydrocarboncarboxylic acids as given above which are substituted by one or more of halogen, nitro, hydroxy, amino, cyano, or thiocyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcyclic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate); and the like.

The acylated compounds, as described above, can be used in animals for the same biological purposes as disclosed above for U-58,431. For example, the acylated compounds can be given in oral form to an animal possessing the necessary enzyme to remove the acyl group, thus freeing the parent antibiotic compound which then inhibits susceptible bacteria.

We claim:

1. Antibiotic U-58,431 which can be shown by the following formula:

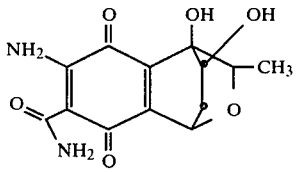

and base addition salts thereof.

2. Tetra-acylates of antibiotic U-58,431, which can be shown by the following formula:

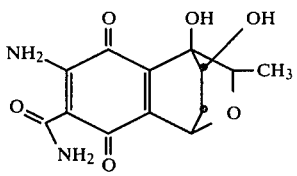

wherein the amino and hydroxyl groups are acylated, said acyl group consists of a hydrocarbon carboxylic acid acyl of from 2 to 18 carbon atoms, inclusive; halo-, nitro-, hydroxy-, amino-, cyano-, thiocyano-, and lower alkoxy-substituted hydrocarbon carboxylic acid acyl of from 2 to 18 carbon atoms, inclusive.

3. Di-O-acylates of antibiotic U-58,431, which can be shown by the following formula:

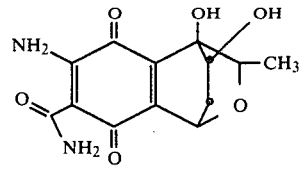

wherein the hydroxyl groups are acylated, said acyl group consists of a hydrocarbon carboxylic acid acyl of from 2 to 18 carbon atoms, inclusive; halo-, nitro-, hydroxy-, amino-, cyano-, thiocyano-, and lower alkoxysubstituted hydrocarbon carboxylic acid acyl of from 2 to 18 carbon atoms, inclusive.

4. Di-N-acylates of antibiotic U-58,431, which can be shown by the following formula:

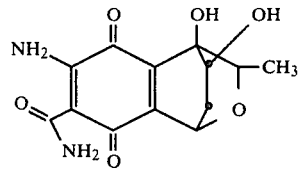

wherein the amino groups are acylated, said acyl group consists of a hydrocarbon carboxylic acid acyl be from 2 to 18 carbon atoms, inclusive; halo-, nitro-, hydroxy-, amino-, cyano-, thiocyano-, and lower alkoxysubstituted hydrocarbon carboxylic acid acyl of from 2 to 18 carbon atoms, inclusive.

* * * * *